United States Patent [19]

Combs et al.

[11] Patent Number: 5,522,827
[45] Date of Patent: Jun. 4, 1996

[54] APPARATUS AND METHOD FOR HARVESTING A TENDON GRAFT

[75] Inventors: Charles R. Combs, Lexington, Ky.; Kevin S. Cook, Winona Lake; Charles D. Persons, Columbia City, both of Ind.

[73] Assignee: Zimmer, Inc., Warsaw, Ind.

[21] Appl. No.: 232,547

[22] Filed: Apr. 22, 1994

[51] Int. Cl.$^6$ .................................................. A61B 19/00
[52] U.S. Cl. ........................................................... 606/167
[58] Field of Search ................................... 606/1, 45, 79, 606/110, 113, 138, 139, 144–148, 150, 167, 170, 222, 223, 224, 225, 228

[56] References Cited

U.S. PATENT DOCUMENTS

| | | | |
|---|---|---|---|
| 4,509,516 | 4/1985 | Richmond . | |
| 4,773,417 | 9/1988 | Moore et al. . | |
| 4,781,191 | 11/1988 | Thompson . | |
| 4,901,717 | 2/1990 | Moore et al. . | |
| 4,966,600 | 10/1990 | Songer et al. . | |
| 5,108,406 | 4/1992 | Lee | 606/113 |
| 5,129,912 | 7/1992 | Noda et al. | 606/139 |
| 5,192,321 | 3/1993 | Strokon . | |
| 5,234,445 | 8/1993 | Walker et al. | 606/139 |
| 5,284,485 | 2/1994 | Kammerer et al. . | |
| 5,312,416 | 5/1994 | Spaeth et al. | 606/110 |
| 5,336,231 | 8/1994 | Adair | 606/1 |
| 5,387,219 | 2/1995 | Rappe | 606/1 |
| 5,417,684 | 5/1995 | Jackson et al. | 606/113 |

OTHER PUBLICATIONS

Zimmer, Inc.—Bunnell Tendon Strippers—Catalog p. B71, Rev. 1—Feb. 1973.
Linvatec, Corp.—Concept Tendon Harvester—Catalog pp. 72, 102—1992.
Linvatec, Corp.—Concept ACL/PCL Graft Passer—Catalog p. 71—1992.
3M Health Care ad—Agee Carpal Tunnel Release System—1994.

Primary Examiner—Stephen C. Pellegrino
Assistant Examiner—Glenn Dawson
Attorney, Agent, or Firm—Margaret L. Geringer

[57] ABSTRACT

An apparatus and method for harvesting a tendon graft beneath the overlying tissues through a remote incision which exposes only a portion of the donor tendon from which the graft will be harvested. The apparatus or tendon harvester 10 includes an elongated tubular shaft 20 connected to a cylindrical handle 30 and a length of flexible cutting wire or cable 12. A needle 16 is connected to one end of the cable 12 which extends from the distal end of the shaft 20. The needle end of the cable 12 is affixed to the distal end of the shaft 20 to form a cable loop for slitting the tendon 4. The method using the harvester 10 includes: making an incision to expose only a portion of said donor tendon at the proximal end of the tendon graft to be harvested; slitting or stripping said donor tendon longitudinally to form the tendon graft by passing the cable loop laterally through or around the donor tendon and the moving the cable loop along the donor tendon beneath the overlying tissue; and severing said tendon graft at its distal end beneath the overlying tissue by closing the cable loop.

12 Claims, 6 Drawing Sheets

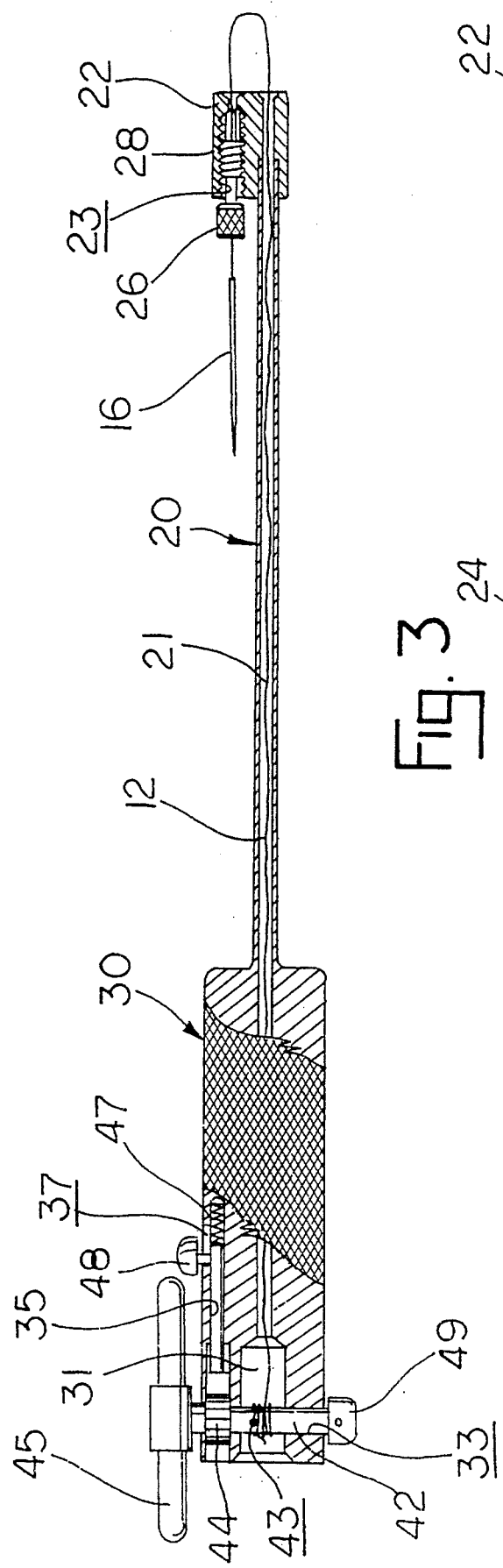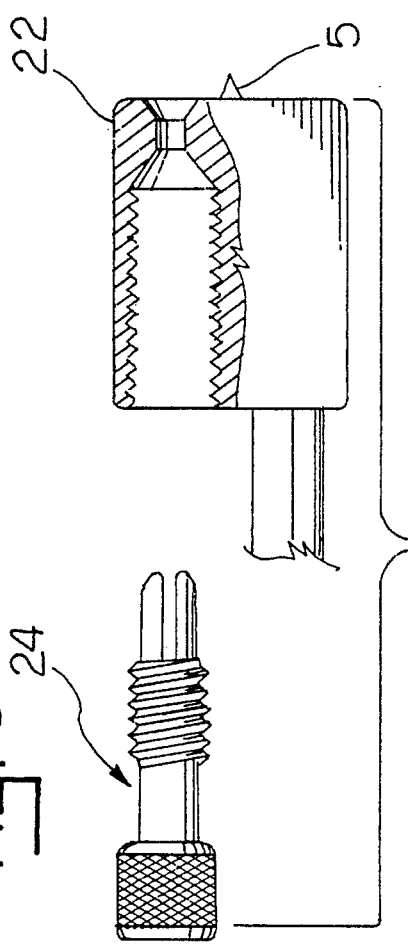

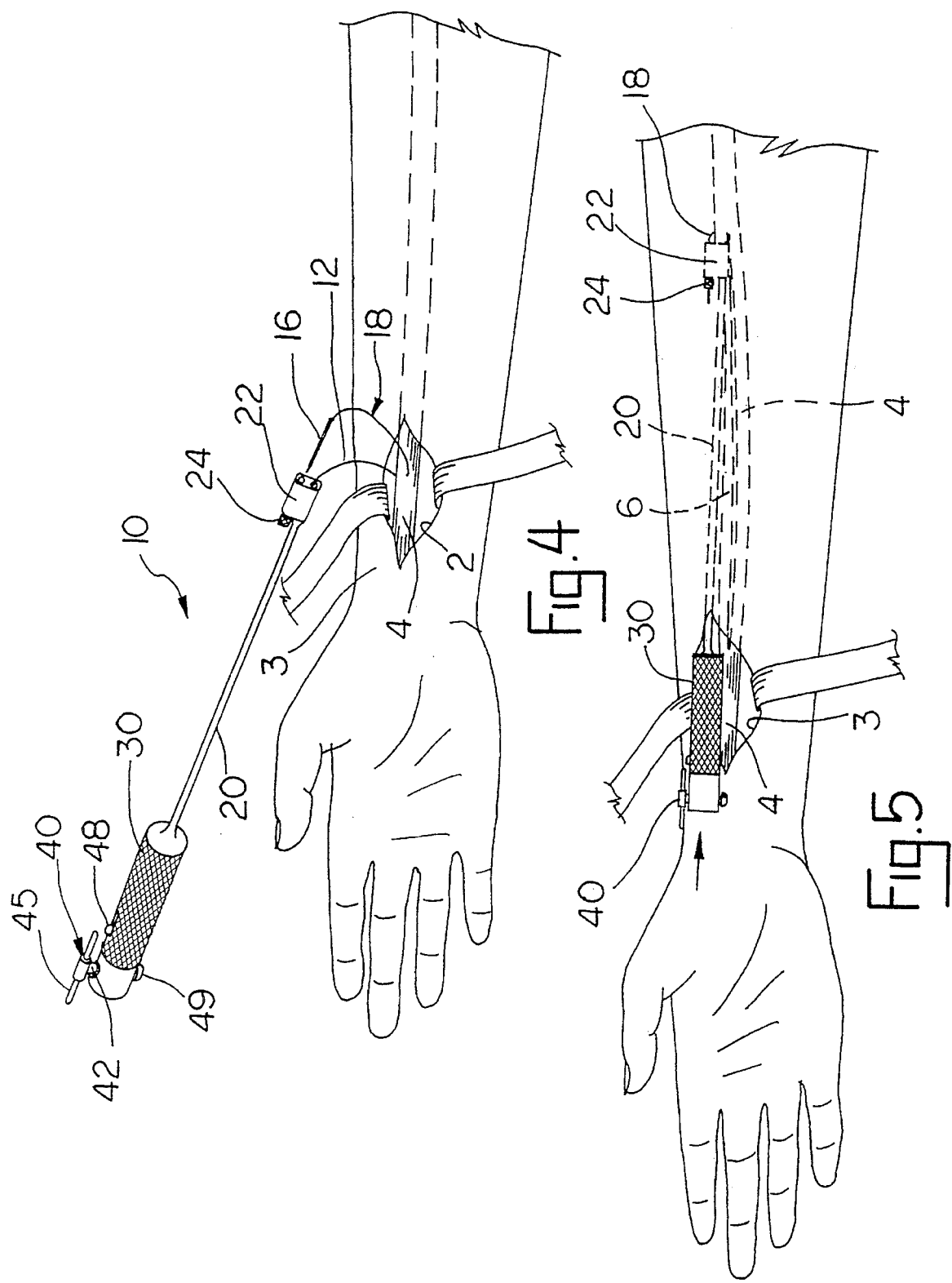

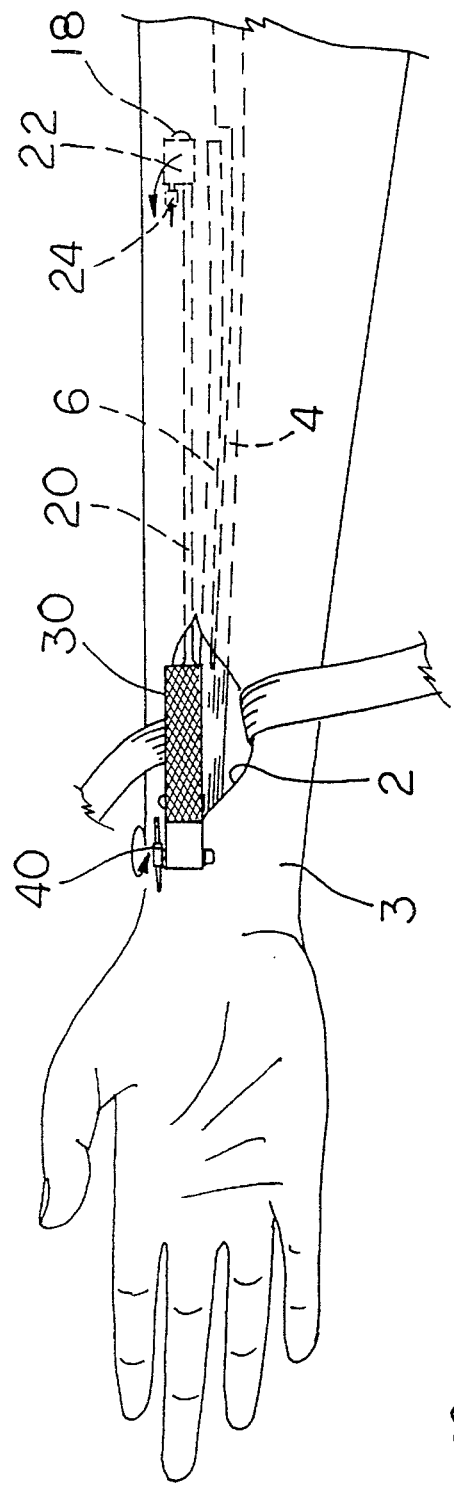

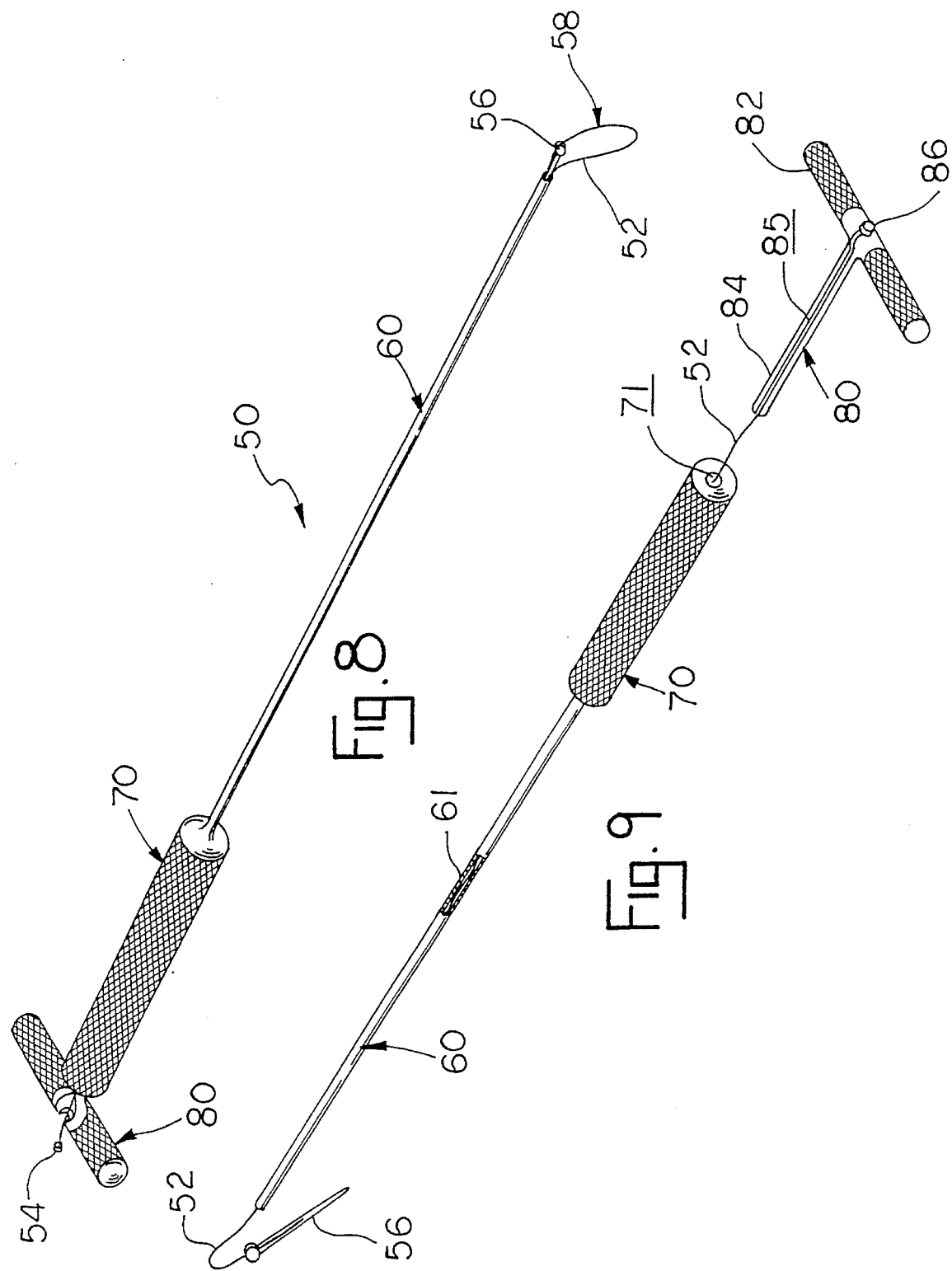

APPARATUS AND METHOD FOR HARVESTING A TENDON GRAFT

This invention relates to a surgical apparatus for harvesting a tendon graft and method for using the same, and in particular an apparatus used to harvest a tendon graft from beneath the overlying tissue through a remote incision.

BACKGROUND OF INVENTION

Surgical procedures for harvesting portions of tendons or grafts for use in the reconstruction of joints are well known. Since tendons are a fibrous tissue, tendon grafts are obtained by stripping a length of tendon tissue longitudinally from a donor tendon. Harvesting a tendon graft or tenectomy may involve making an incision to expose the entire length of donor tendon from which the tendon graft will be taken. The donor tendon is longitudinally slit or stripped by a bladed instrument or a tendon stripper. The ends of the tendon graft are severed and the graft removed. Alternatively, a small incision is made to expose the donor tendon at one end of the intended graft and another incision is made to expose the donor tendon at the opposite end of the graft. The tendon is then slit by a stripper which is passed under the skin along the donor tendon. The ends of the tendon graft are severed through the two small incisions. While making two smaller incisions may lessen the tissue trauma and scarring, locating the donor tendon through the second incision is often difficult. In addition, the surgeon must determine which portion of the tendon tissue is the graft before severing the ends.

It is also known to strip a tendon and then sever just one end of the tendon while the other end remains naturally attached. The severed end is then repositioned and reattached at the desired new location. Such a procedure for the knee is disclosed by U.S. Pat. Nos. 4,901,717 and 4,773,417 to Moore et al. In addition, an instrument is available called the Concept Tendon Harvester which is sold by Linvatec, Corp. The Concept Tendon Harvestor utilizes two elongated concentric tubular members. The inner member can be rotated within the outer member to provide three positions: an open position enabling the tendon to be inserted into an opening in the distal end of the instrument; a locked position which holds the tendon during the stripping process; and a cutting position in which a cutting edge on the inner tubular member is rotated to cut the tendon at the remote end of the tendon. The graft can then be harvested with or without cutting the other end of the tendon at the incision site, at the surgeon's discretion.

SUMMARY OF INVENTION

The tendon harvester of this invention and its method of use provide advantages over conventional tendon strippers in lessening tissue trauma and simplifying the harvesting procedure. The tendon harvester can be used to harvest the tendon beneath the overlying tissues through a remote incision which exposes only a portion of the donor tendon. The tendon harvester of this invention includes an elongated tubular shaft connected to a cylindrical handle and a length of flexible cutting wire or cable. A needle or pin is connected to one end of the cable which extends from the distal end of the shaft. This distal needle end of the cable is affixed to the distal end of the shaft to form a cable loop for slitting or stripping the tendon. In the preferred embodiment of the harvester, the distal end of the shaft includes a head part which is adapted for restrictively receiving the needle to form a cable loop. The opposite end of the cable is connected to a winder housed in the handle. In an alternative embodiment of the harvester, the taper of the needle allows it to be lodged in the shaft bore to form the cable loop. The opposite end of the cable is connected to an extensible T-shaped handle inserted in the cylindrical handle.

In use, an incision is made to expose only a portion of the donor tendon. The needle and connected cable are inserted laterally through or around the tendon. If a longitudinal strip or section of the tendon is to harvested, the needle and attached cable are inserted laterally through the tendon (as shown in FIGS. 4–6). If it is desired to harvest a whole portion of the tendon, the needle and attached tissue would be passed laterally around the tendon to enable the tendon to be separated or stripped away from any adjacent tissue. The needle is connected to the distal end of the shaft to form the cutting loop. The distal end of the harvester is then moved longitudinally up the tendon through the incision beneath the overlying tissues and skin. As the distal end of the harvester moves along the tendon, the cable loop slits or strips the tendon. Once the approximate length of tendon graft has been slit, the cable loop is closed or drawn tight by rotating the winder or pulling the T-handle. Drawing the cable loop closed severs the distal end of the tendon graft from the donor tendon underneath the overlying tissue. Alternatively, a cutting edge or cutting blade may be provided at the distal end of the instrument to help cut the distal end of the tendon graft. The harvester is then removed. The proximal end of the tendon grafted is severed at the incision and the graft removed through the single incision. Using this method, a tendon graft of various lengths can be harvested from beneath the overlying tissue through a single remote incision, which lessens tissue trauma and reduces the likelihood of infection. Thus, with the present invention, there is no need for a second incision, thus preventing additional scarring and other potential complications from a second incision.

Accordingly, an advantage of this invention is to provide for an apparatus for harvesting a tendon graft.

Another advantage is to provide for a tendon harvester which includes an elongated tubular shaft connected to a cylindrical handle and a length of flexible cutting wire or cable connected to the distal end of the shaft to form a collapsible cutting loop.

Another advantage is to provide a method for harvesting a tendon graft using an apparatus which allows the graft to be harvested from beneath the overlying tissue through a single remote incision without exposing the entire length of donor tendon.

Other advantages will become apparent upon a reading of the following description.

BRIEF DESCRIPTION OF THE DRAWINGS

A preferred embodiment of the invention has been depicted for illustrative purposes only wherein:

FIG. 3 is a side view of the tendon harvester of FIG. 1 shown with partial sectional views of the handle and shaft.

FIG. 3A is an enlarged exploded view of the distal tip of the harvester of FIG. 1 with a modification on the tip.

FIG. 4 is a perspective view of a forearm and the harvester of FIG. 1 showing the distal needle end of the cable inserted into an incision and passing through the exposed donor tendon.

FIG. 5 is a perspective view of the forearm and the harvester of FIG. 4 showing the distal end of the harvester inserted through the incision beneath the tissue and showing the cable loop slitting the donor tendon to form the tendon graft.

FIG. 6 is a perspective view of the forearm and harvester of FIG. 4 showing the distal end of the harvester inserted through the incision beneath the tissue and showing the cutting cable loop drawn closed to sever the tendon graft at its distal end.

FIG. 7 is a perspective view of the forearm and harvester of FIG. 4 showing the distal end of the harvester removed from the incision with the tendon graft ready to be severed at its proximal end.

FIG. 8 is a perspective view of a second embodiment of the tendon harvester of this invention with the needle inserted into the distal end of the shaft.

FIG. 9 is an exploded view of the second embodiment of the tendon harvester showing the extensible T-handle, the cutting cable and the needle.

DESCRIPTION OF THE PREFERRED EMBODIMENT

The preferred embodiments herein described are not intended to be exhaustive or to limit the invention to the precise form disclosed. It is chosen and described to explain the principles of the invention and its application and practical use to enable others skilled in the art to utilize its teachings.

Figure 1:
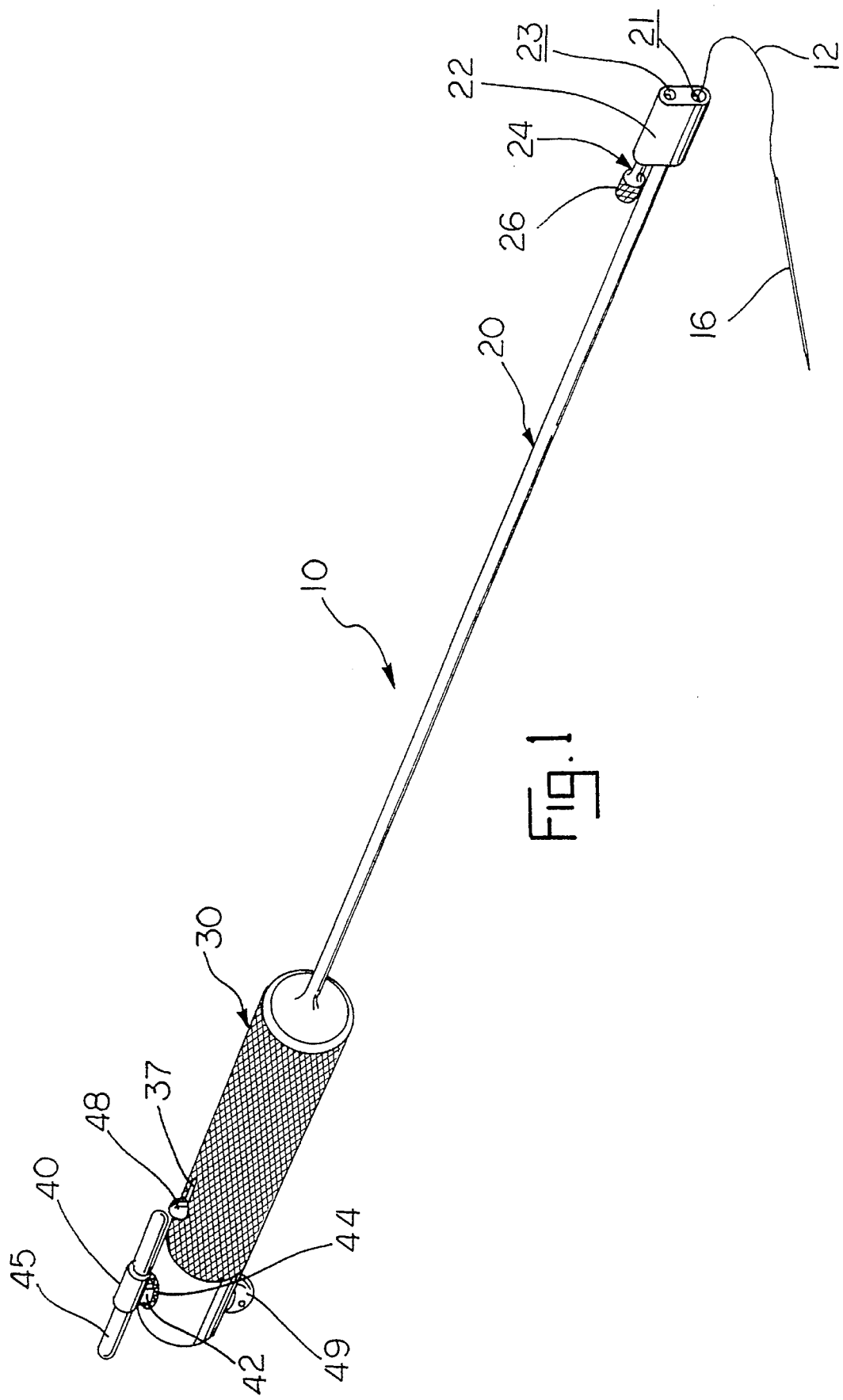
FIG. 1 is perspective view of one embodiment of the tendon harvester of this invention.
Figure 2:
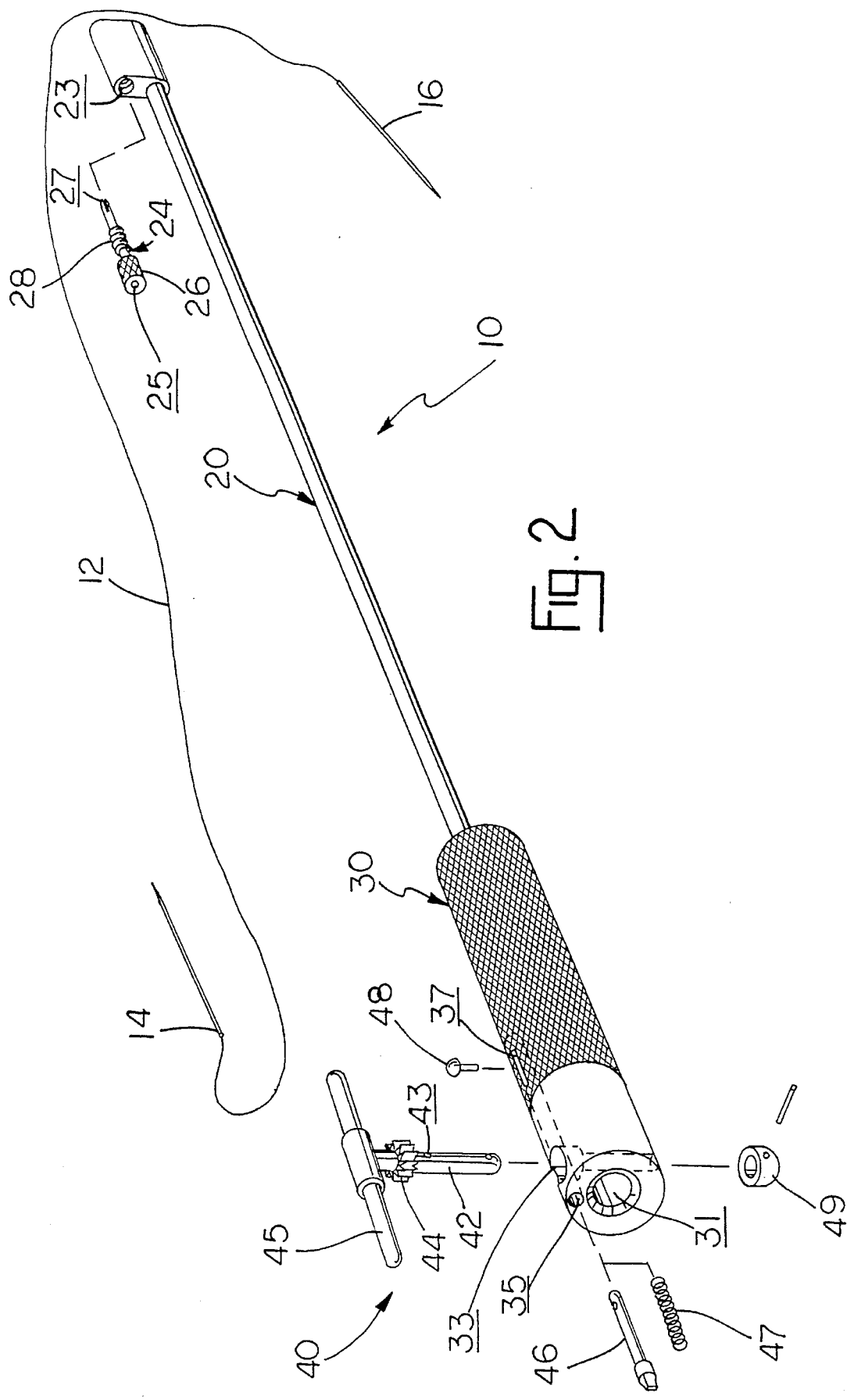
FIG. 2 is an exploded view of the tendon harvester of FIG. 1.

FIGS. 1–3 show the preferred embodiment of the tendon harvester 10 of this invention. Harvester 10 includes an elongated tubular shaft 20 connected to a hollow cylindrical handle 30 and a length of flexible wire or cable 12. Handle 30 has an axial central bore 31 which extends the length of the handle and aligns with axial bore 21 of shaft 20. Cable 12 passes through central bore 31 of handle 30 and axial bore 21 of shaft 20. One end of the cutting cable 12 is connected to a winder 40 housed within handle 30 and the opposite end extends from the distal end of shaft 20. Cable 12 has needles 14 and 16 connected to each end. The one needle 14 is connected to the proximal end of the cable which is attached to the winder 40, while the other needle 16 is connected to the opposite end of cutting cable 12 which extends from the distal end of shaft 20. Having a needle at each end allows the cable to be reversible, and thus enables either end of the cable 12 to be utilized at either end of the instrument. The needles 14 and 16 help to thread the cable 12 through the harvester 10. It is noted that the cable 12 may also be made non-reversible with a needle 16 at one end and an enlarged securing ball (not shown) or other locating means connecting to winder 40 at the other end.

Winder 40 allows the cable 12 to be drawn into the distal end of shaft 20. Handle 30 has a lateral rachet bore 33 which intersects with center bore 31. A longitudinal plunger bore 35 is formed in the handle parallel and off centered to center bore 31. Rachet bore 33 and plunger bore 35 intersect as shown in FIGS. 2 and 3. A winder rod 42 is rotatably housed within rachet bore 33 and extends partially from both sides of handle 30. Rod 42 has a lateral bore 43 for receiving the proximal needle end 14 of cutting cable 12, such that cable 12 extends through hole 43. Rod 43 further includes an annular toothed rachet 44. A crank arm 45 is connected to one end of rod 42 for rotating the rod inside rachet bore 33 and a cap 49 is connected to the opposite end. Manually turning crank arm 45 wraps cable 12 around rod 42 which draws the distal needle end of cable 12 into the distal end of shaft 20. As shown in FIGS. 2 and 3, rachet 44 is positioned at the intersection of rachet bore 33 and plunger bore 35. A plunger 46 is shiftably disposed in plunger bore 35. A spring 47 urges the head of plunger 46 into engagement with rachet 44. A release knob 48 is connected to plunger 46 through a slot 37 in handle 30. The engagement of plunger 46 against rachet 44 allows rod 42 to be rotated in only one direction which prevents cable 12 from being unwound from rod 42. Once the cable 12 has been wrapped around rod 42 several times to secure the cable 12 to rod 42, the needle 14 may be cut or removed from the cable 12 (as shown in FIG. 3), so that needle 14 is not dangling from the end of the harvester 10. Manually shifting knob 48 away from crank arm 45 disengages plunger 46 from rachet 44 which allows rod 42 to be rotated in the opposite direction so that cable 12 can be unwound from rod 42.

A head part 22 is integrally connected to the distal end of shaft 20. Head part 22 has a partially threaded lock bore 23 which parallels axial bore 21 of shaft 20. A lock screw 24 is turned into lock bore 23 of head part 22. Lock screw 24 includes a knurled head 26 and a threaded body 28. Lock screw 24 has an axial bore 25 for receiving distal needle 16. The distal end of lock screw 24 has four cross slits 27 which may be tapered at the tip of the distal end of the lock screw which allow bore 25 to be constricted when turned into lock bore 23 thereby securing needle 16 to head part 22. The cross slits 27 constrict to tighten about needle 16 or cable 12 when cross slits 27 are turned into the tapered portion of lock bore 23.

FIGS. 4–7 shows harvester 10 used to harvest a tendon graft from a forearm for the surgical reconstruction of a hand. A small incision 2 is made in the skin 3 to expose a portion of the donor tendon 4. It should be noted that the majority of the donor tendon from which the tendon graft will be taken is not exposed by incision 2 and that the exposed portion of the donor tendon constitutes only the proximal end of the tendon graft to be harvested. As shown in FIG. 4, needle 16 is inserted laterally through donor tendon 4 and cable 12 is drawn through the donor tendon. Needle 16 is connected to head part 22 so that cable 12 forms a collapsible cutting loop 18 which passes through donor tendon 4. Needle 16 is inserted into lock screw 24 which is loosely turned into bore 23. Lock screw 24 is turned down to secure cable 12 to head part 22. Any excess length of needle 16 or cable 12 which extends beyond lock screw 24 is clipped off by any suitable method. If desired, the length of cable 12 forming cutting loop 18 can be reduced by rotating crank arm 45 to wrap cable 12 around rod 42. As shown in FIG. 5, the distal end of shaft 20 is inserted into incision 2 following donor tendon 4 beneath the skin. As the distal end of shaft 20 moves along the donor tendon, cutting loop 18 slits the tendon with one segment to become the tendon graft 6. Once donor tendon 4 has been longitudinally slit to provide tendon graft 6 of sufficient length, the distal end of tendon graft 6 is severed from donor tendon 4. It is noted that a scale (not shown) could be provided along shaft 20 to indicate the distance from the distal end of shaft 20 to indicate the approximate length of the tendon graft 6. As shown in FIG. 6, the distal end of tendon graft 6 is severed by rotating crank arm 45 which retracts cable 12 into the distal end of the shaft and closes cutting loop 18. Closing the cutting loop severs the tendon graft at the distal end beneath the skin. Alternatively, a cutting edge or cutting blade 5 (as shown in FIG. 3A) could be provided at the distal end of the instrument extending from head part 22 to help cut the distal end of the tendon graft. The cable 12 could be retracted to close the cutting loop toward blade 5 to trap the tendon graft therebetween to sever the distal end of the tendon graft. Other supplemental cutting mechanisms could be provided, such as a retractable cutting blade (not shown) or other suitable cutting aids. Ideally, the cutting mechanism would be such a retractable or otherwise protected blade rather than a blade which was always exposed, in order to lessen the tissue damage while stripping or moving along the tendon. Shaft 20 is then withdrawn from the incision. As shown in FIG. 7, the proximal end of tendon graft 6 is severed by any suitable method, such as scissors 8, and the newly resected tendon graft is removed through the incision by forceps (not shown).

FIGS. 8 and 9 show a second embodiment of the tendon harvester 50 of this invention. Harvester 50 includes an elongated tubular shaft 60, a handle 70 connected to the proximal end of shaft 60, an extensible T-shaped handle 80 and a length of flexible cutting cable 52. Handle 70 has a central bore 71 which extends the length of the handle and aligns with an axial bore 61 of shaft 60. T-handle 80 is shiftably housed within center bore 71. T-handle 80 includes a neck 84 and a cross member 82. One end of the cutting cable 52 is connected to T-handle 80. A ball 54 is connected to the handle end of cable 52. Cable 52 fits into a slot 85 in neck 84 with the ball end of cable 52 resting in a counterbore 86. The opposite end of the cutting cable passes through handle 70 and shaft 60 and extends from the distal end of shaft 60. A needle 56 is connected to the end of cutting cable 52 extending from the distal end of the shaft. Needle 56 has a longitudinal taper with the diameter of the proximal end being slightly greater than that of the diameter of axial bore 61 of shaft 60.

In use, tendon harvester 50 operates substantially as described above. The needle 56 is inserted laterally through the donor tendon and cable 52 is drawn through the donor tendon. Then needle 56 is inserted back into bore 61 at the distal end of shaft 60 to form a collapsible cutting loop 58 as shown in FIG. 8. The taper of needle 56 engages the walls of bore 61 of the shaft to secure needle 56 within bore 61 at the distal end of the shaft. The distal end of shaft 60 is inserted into the incision following the tendon. Cutting loop 58 slits the donor tendon as the distal end moves under the skin along the donor tendon. When the proper length of the graft has been slit, the surgeon protracts T-handle 80 from handle 70 thereby pulling cable 52 into the distal end of shaft 60 and closing cable loop 58. A slot is provided along the length of the needle to enable cable 52 to slide along the slot of the inserted needle 56 as the cross-member 82 of T-handle 80 is pulled out or away from handle 70. Closing the cable loop severs the distal end of the tendon graft. The shaft is withdrawn from the incision. The proximal end of the tendon graft is severed by any suitable method and the newly resected tendon graft is removed through the incision.

It is noted that the tendon harvester of the present invention may be manufactured by any suitable manufacturing method. The tendon harvester may be made of stainless steel, although any suitable material may be utilized. Any suitable diameter and strength of cable or wire may be utilized, as desired.

While the method of using the preceding embodiments of the tendon harvester have been illustrated in resecting a tendon graft from a forearm, it will be understood that the apparatus and techniques described are applicable for harvesting tendon grafts from other parts of the body, the harvester's geometry being adjusted accordingly. Likewise, it is understood that the above description does not limit the invention to the details given, but may be modified within the scope of the following claims.

I claim:

1. An apparatus for harvesting a tendon graft from a donor tendon comprising:

an elongated tubular shaft having a bore defined between its distal end and its proximal end, a cable shiftably carried within said shaft bore and having a first end and a second end, said cable first end extending partially from said shaft distal end and being adapted to pass laterally through or around said donor tendon, means connected to said shaft distal end for attaching said cable first end to said shaft distal end whereby said cable first end forms a cable loop at said shaft distal end for longitudinally slitting or stripping said donor tendon to form said tendon graft, and retracting means carried by said shaft and connected to said cable second end for pulling said cable into said shaft bore thereby closing said cable loop at said shaft distal end to sever one end of said tendon graft, and wherein said retracting means includes a rod part rotatably housed within said shaft proximal end and a lock means for preventing rotational movement of said rod part within said shaft proximal end, said cable second end connected to said rod part whereby rotation of said rod part wraps said cable around said rod part and pulls said cable into said shaft bore at said shaft distal end to close said cable loop.

2. An apparatus for harvesting a tendon graft from a donor tendon comprising:

an elongated tubular shaft having a bore defined between its distal end and its proximal end, a cable shiftably carried within said shaft bore and having a first end a second end, said cable first end extending partially from said shaft distal end and being adapted to pass laterally through or around said donor tendon, means connected to said shaft distal end for attaching said cable first end to said shaft distal end whereby said cable first end forms a cable loop at said shaft distal end for longitudinally slitting or stripping said donor tendon to form said tendon graft, and retracting means carried by said shaft and connected to said cable second end for pulling said cable into said shaft bore thereby closing said cable loop at said shaft distal end to sever one end of said tendon graft, and wherein said attaching means includes a head part on said shaft distal end and having a head part bore defined therein, and a lock screw fitted into said head part bore, said lock screw is adapted for receiving said cable first end in constrictive engagement to connect said cable first end to said head part, wherein said cable first end includes a needle means for laterally piercing said donor tendon.

3. An apparatus for harvesting a tendon graft from a donor tendon comprising:

an elongated tubular shaft having a bore defined between its distal end and its proximal end, a cable shiftably carried within said shaft bore and having a first end a second end, said cable first end extending partially from said shaft distal end and being adapted to pass laterally through or around said donor tendon, means connected to said shaft distal end for attaching said cable first end to said shaft distal end whereby said cable first end forms a cable loop at said shaft distal end for longitudinally slitting or stripping said donor tendon to form said tendon graft, and retracting means carried by said shaft and connected to said cable second end for pulling said cable into said shaft bore thereby closing said cable loop at said shaft distal end to sever one end of said tendon graft, and wherein said shaft distal end further includes a cutting blade to help sever said tendon graft.

4. An apparatus for harvesting a tendon graft from a donor tendon comprising:

an elongated tubular shaft having a bore defined between its distal end and its proximal end, a cable shiftably said shaft bore and having a first end and a second end, said cable first end extending partially from said shaft distal end and being adapted to pass laterally through or around said donor tendon, means connected to said shaft distal end for attaching said cable first end to said shaft distal end whereby said cable first end forms a cable loop at said shaft distal end for longitudinally slitting or stripping said donor tendon to form said tendon graft, and retracting means carried by said shaft and connected to said cable second end for pulling said cable into said shaft bore thereby closing said cable loop at said shaft distal end to sever one end of said tendon graft, and wherein said cable first end includes a needle means for laterally piercing said donor tendon, and wherein said needle means also constitutes part of said attaching means and said needle means includes a tapered body which restrictively engages said shaft distal end within said bore when said needle means is inserted into said bore at said shaft distal end, and wherein said needle means includes an elongated slot to enable the cable to slide along the slot as the cable is retracted.

5. The apparatus of claim 4 wherein said retracting means includes a handle part shiftably disposed within said shaft bore adjacent said shaft proximal end for longitudinal movement toward and away from said shaft distal end, said cable second end connected to said handle part whereby extensible movement of said handle part away from said shaft distal end pulls said cable into said shaft distal end to close said cable loop.

6. An apparatus for harvesting a tendon graft from a donor tendon comprising:

an elongated tubular shaft having a bore defined between its distal end and its proximal end, a cable shiftably carried within said shaft bore and having a first end and a second end, said cable first end extending partially from said shaft distal end and being adapted to pass laterally through said donor tendon, a needle part connected to said cable first end and constituting means for laterally piercing said donor tendon, a head part on said shaft distal end and having a head part bore, a lock screw fitted into said head part bore and being adapted for connecting said needle part to said head part whereby said cable first end forms a cable loop at said shaft distal end for longitudinally slitting said donor tendon to form said tendon graft, and a winder part rotatably housed within said shaft proximal end, said cable second end connected to said winder part whereby rotation of said winder part wraps said cable around said winder part and pulls said cable into said shaft bore to close said cable loop at said shaft distal end thereby severing one end of said tendon graft.

7. The apparatus of claim 6 wherein said head part further includes a cutting blade to help sever said tendon graft.

8. An apparatus for harvesting a tendon graft from a donor tendon comprising:

an elongated tubular shaft having a bore defined between its distal end and its proximal end, a cable shiftably carried within said shaft bore and having a first end and a second end, said cable first end extending partially from said shaft distal end and being adapted to pass laterally through said donor tendon, a needle part connected to said cable first end and constituting means for laterally piercing said donor tendon, said needle part being insertable into said shaft bore at said shaft distal end whereby said cable first end forms a cable loop at said shaft distal end for longitudinally slitting said donor tendon to form said tendon graft, and wherein said needle part includes an elongated slot, a handle part shiftably disposed within said shaft bore adjacent said shaft proximal end for longitudinal movement toward and away from said shaft distal end, said cable second end connected to said handle part whereby extensible movement of said handle away from said shaft distal end pulls said cable into said shaft distal end and along said slot in said needle part to close said cable loop when said needle part is connectively inserted into said shaft bore at said shaft distal end.

9. A method for harvesting a tendon graft from a donor tendon beneath the overlying tissue and skin through a remote incision comprising the steps of:

a. making an incision to expose only a portion of said donor tendon at a proximal end of the tendon graft to be harvested;

b. slitting or stripping said donor tendon longitudinally beneath the overlying tissue with a tendon harvester to form said tendon graft;

c. severing said tendon graft with said tendon harvester at a distal end of the tendon graft beneath the overlying tissue; and wherein the step of slitting or stripping said donor tendon is performed with said tendon harvester including an elongated tubular shaft having a bore defined between its distal end and its proximal end, a cable shiftably carried within said shaft bore and having a first end and a second end, said cable first end extending partially from said shaft distal end and being adapted to pass laterally through or around said donor tendon, and further includes the steps of passing said cable first end laterally through or around said donor tendon at said incision; connecting said cable first end to said shaft distal end to form a cable loop around part of said donor tendon; and inserting said shaft distal end through said incision and longitudinally along said donor tendon beneath the overlying tissue whereby said cable loop longitudinally slits or strips said donor tendon to form said tendon graft.

10. The method of claim 9 further including the steps of severing said tendon graft at a proximal end of the tendon graft through said incision; and extracting said tendon graft from said incision.

11. The method of claim 10 wherein the step of severing the tendon graft at its distal end is performed with said tendon harvester, said tendon harvester also includes retracting means carried at said shaft proximal end and connected to said cable second end for pulling said cable into said shaft bore thereby closing said cable loop formed at said shaft distal end when said first end is connected to said shaft distal end, and further includes the step of closing said cable loop when said shaft distal end is inserted beneath the overlying tissue to sever said tendon graft at its distal end.

12. The method of claim 11 wherein the step of severing the tendon graft at its distal end with said tendon harvester further includes providing the shaft distal end of the tendon harvester with a cutting blade, and further includes the step of closing said cable loop toward said cutting blade when said shaft distal end is inserted beneath the overlying tissue to help sever said tendon graft at its distal end.

* * * * *